(12) United States Patent
Lee et al.

(10) Patent No.: US 12,358,854 B2
(45) Date of Patent: Jul. 15, 2025

(54) METHOD AND APPARATUS FOR CONVERTING HYDROCARBON-BASED MATERIAL INTO ACETYLENE OR ETHYLENE

(71) Applicant: KOREA INSTITUTE OF MACHINERY & MATERIALS, Daejeon (KR)

(72) Inventors: Dae-hoon Lee, Daejeon (KR); Duy Khoe Dinh, Daejeon (KR); Hong Jae Kang, Daejeon (KR); Kwan-Tae Kim, Daejeon (KR); Hohyun Song, Daejeon (KR); You-Na Kim, Daejeon (KR); Heesoo Lee, Daejeon (KR); Younghoon Song, Daejeon (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 319 days.

(21) Appl. No.: 17/904,764

(22) PCT Filed: Mar. 16, 2021

(86) PCT No.: PCT/KR2021/003264
§ 371 (c)(1),
(2) Date: Aug. 22, 2022

(87) PCT Pub. No.: WO2021/187879
PCT Pub. Date: Sep. 23, 2021

(65) Prior Publication Data
US 2023/0045639 A1    Feb. 9, 2023

(30) Foreign Application Priority Data
Mar. 16, 2020 (KR) .......................... 10-2020-0032134

(51) Int. Cl.
*C07C 2/84* (2006.01)
*B01J 19/00* (2006.01)
(Continued)

(52) U.S. Cl.
CPC ............. *C07C 2/84* (2013.01); *B01J 19/0013* (2013.01); *B01J 19/088* (2013.01); *C07C 5/05* (2013.01);
(Continued)

(58) Field of Classification Search
CPC .... C07C 2/84; C07C 5/05; C07C 2/80; C07C 2/74; C07C 11/04; C07C 11/24;
(Continued)

(56) References Cited

U.S. PATENT DOCUMENTS 5,749,937 A * 5/1998 Detering .................. H05H 1/34
75/10.21
5,993,761 A * 11/1999 Czernichowski ...... H05H 1/482
204/173
(Continued)

FOREIGN PATENT DOCUMENTS

| CN | 1182456 | 5/1998 |
| CN | 1478765 | 3/2004 |

(Continued)

OTHER PUBLICATIONS

EPO, Extended European Search Report and Written Opinion of the corresponding European Patent Application No. 21770870.0., dated May 16, 2024, total 10 pages.

*Primary Examiner* — Ali Z Fadhel
(74) *Attorney, Agent, or Firm* — LEX IP MEISTER, PLLC

(57) ABSTRACT

A method of converting a hydrocarbon-based material into acetylene or ethylene according to an embodiment of the present invention includes a supply step of supplying a
(Continued)

gaseous or liquid hydrocarbon-based material to a plasma reactor, and a temperature control step of creating a temperature condition of a decomposition reaction of converting the hydrocarbon-based material into acetylene or ethylene in a reaction space in the plasma reactor.

19 Claims, 11 Drawing Sheets

(51) Int. Cl.
  B01J 19/08 (2006.01)
  C07C 5/05 (2006.01)
(52) U.S. Cl.
  CPC .................. *B01J 2219/0809* (2013.01); *B01J 2219/0871* (2013.01)
(58) Field of Classification Search
  CPC .................. B01J 19/0013; B01J 19/088; B01J 2219/0809; B01J 2219/0871; B01J 2219/083; B01J 2219/0875; B01J 2219/0877; H05H 1/34; Y02P 20/52
  See application file for complete search history.

(56) References Cited

U.S. PATENT DOCUMENTS

| | | | |
|---|---|---|---|
| 6,326,407 B1 * | 12/2001 | Eliasson | ............... C10G 50/00 518/715 |
| 2004/0208805 A1 | 10/2004 | Fincke et al. | |
| 2005/0065392 A1 | 3/2005 | Peterson et al. | |
| 2008/0289494 A1 * | 11/2008 | Boutot | ...................... C01B 3/24 95/81 |
| 2009/0038933 A1 * | 2/2009 | Boutot | .................. B01J 19/088 422/186.21 |
| 2014/0058170 A1 * | 2/2014 | Bedard | ..................... B01J 3/008 585/539 |
| 2015/0223314 A1 * | 8/2015 | Hoermann | ............... H05H 1/34 |
| 2016/0194202 A1 * | 7/2016 | Rabinovich | ............ B01J 19/088 422/186.21 |
| 2018/0215616 A1 * | 8/2018 | Cha | ......................... H05H 1/26 |
| 2018/0243721 A1 * | 8/2018 | Manning | ................ B01J 19/088 |
| 2018/0290123 A1 * | 10/2018 | Jovanovic | ............ B01J 19/0093 |
| 2019/0262816 A1 * | 8/2019 | Ha | ............................ B01J 29/90 |
| 2020/0129952 A1 * | 4/2020 | Ha | ............................. C07C 2/82 |
| 2021/0335580 A1 * | 10/2021 | Mislavskij | ......... H01J 37/32449 |

FOREIGN PATENT DOCUMENTS

| | | |
|---|---|---|
| CN | 101282782 | 10/2008 |
| CN | 105669343 | 6/2016 |
| CN | 106414932 | 2/2017 |
| CN | 107827690 | 3/2018 |
| EP | 1413354 | 4/2004 |
| KR | 10-2017-0143079 | 12/2017 |
| KR | 10-2018-0082129 | 7/2018 |
| WO | 9628577 | 9/1996 |

* cited by examiner

METHOD AND APPARATUS FOR CONVERTING HYDROCARBON-BASED MATERIAL INTO ACETYLENE OR ETHYLENE

TECHNICAL FIELD

The present invention relates to a method and apparatus for converting a hydrocarbon-based material into acetylene or ethylene, and more particularly, to a method and apparatus for converting a gaseous or liquid hydrocarbon-based material containing various types of hydrocarbon materials such as methane directly into acetylene or ethylene.

BACKGROUND ART

As well known, ethylene is the essential material used in chemical industries and produced by a naphtha cracker or a gas cracker. These crackers produce ethylene through thermal cracking (pyrolysis) or steam cracking processes and produce an effective yield of ethylene when ethane ($C_2H_6$) and propylene ($C_3H_6$) are mainly used as feed materials.

However, if the feed material is methane, the steam cracking reaction becomes a reforming reaction, which practically makes it impossible to obtain a yield of ethylene.

For this reason, there is a problem in that an indirect process needs to be performed to obtain ethylene by using the feed material containing methane as a main component and the indirect process includes producing synthetic gas in a reforming step and synthesizing ethylene from the synthetic gas.

That is, it is difficult to provide an appropriate temperature condition and reaction time to produce acetylene ($C_2H_2$) or ethylene ($C_2H_4$) by using a feed material only containing methane and hydrogen. A plasma pyrolysis process in the related art mainly produces hydrogen and solid carbon when a feed material is methane.

The plasma pyrolysis process cannot satisfy a condition for producing acetylene or ethylene because of a limitation in that an arc reactor causes an excessively high temperature during a process of producing thermal plasma and the excessively high temperature increases the time it takes to reach a quenching condition.

DISCLOSURE

Technical Problem

The present invention has been made in an effort to provide a method of converting a hydrocarbon-based material into acetylene or ethylene, which produces acetylene or ethylene by converting a supplied hydrocarbon-based material (containing various types of hydrocarbon materials such as methane) directly into acetylene or ethylene. The present invention has also been made in an effort to provide an apparatus for implementing the method.

The present invention has also been made in an effort to provide a method of converting a hydrocarbon-based material into acetylene or ethylene, which is capable of creating a process condition related to a temperature range (e.g., 1,000 to 2,500° C.) and an effective reaction time (e.g., 20 ms or less) of a methane cracking reaction in order to produce acetylene or ethylene in a methane pyrolysis reaction. The present invention has also been made in an effort to provide an apparatus for implementing the method.

Technical Solution

A method of converting a hydrocarbon-based material into acetylene or ethylene according to an embodiment of the present invention includes a supply step of supplying a gaseous or liquid hydrocarbon-based material to a plasma reactor, a temperature control step of creating a temperature condition of a decomposition reaction of converting the hydrocarbon-based material into acetylene or ethylene in a reaction space in the plasma reactor, and a quenching step of inducing a decrease in temperature of the reaction space to maintain the temperature condition for an effective reaction time.

The temperature control step may include creating a temperature condition of the reaction space to 1,000 to 2,500° C.

The quenching step may include maintaining the reaction time to 20 ms or less by quenching the reaction space.

The temperature control step may include creating a temperature condition suitable for a condition for producing acetylene or ethylene by using the fact that a temperature of the reaction space varies depending on a length of a plasma arc when the same electric power is supplied to the plasma reactor to produce the plasma arc.

The temperature control step may include creating a temperature condition that is as low as possible and satisfies a temperature condition equal to or higher than a preset temperature required to convert methane into acetylene or ethylene.

In the temperature control step, alternating current power or direct current power may be applied to a high-voltage electrode and a ground electrode of the plasma reactor, and a length of a plasma arc may further increase when the alternating current power is applied than when the direct current power is applied. The temperature control step may include stabilizing the plasma arc by means of a rotational momentum of electric discharge gas by supplying the electric discharge gas with swirling flow for the plasma arc.

The temperature control step may include anchoring the plasma arc to an inner passageway of the ground electrode so that a length of the plasma arc is maintained with elongated length.

The quenching step may include decreasing a temperature of a reaction field formed in the reaction space to prevent the decomposition reaction from being continuously performed.

The quenching step may be performed by cooling a wall surface of the reaction space and include increasing the amount of cooling by further increasing a surface area of the reaction space than a volume of the reaction space.

In the quenching step, a temperature of the reaction field may be a minimum temperature capable of maintaining the decomposition reaction, and a temperature of a reaction emission may be lowered to a temperature equal to or lower than a temperature that enables the decomposition reaction to be performed by a structure or fluid-dynamics method of the plasma reactor at an end of the reaction field.

A method of converting a hydrocarbon-based material into acetylene or ethylene according to an embodiment of the present invention may include a conversion step of converting the gaseous or liquid hydrocarbon-based material passing through the supply step, the temperature control step, and the quenching step into acetylene or ethylene; and an ethylene yield raising step of raising a yield of ethylene by performing catalytic hydrogenation on the produced acetylene.

The ethylene yield raising step may include a heat exchange step of creating a temperature condition suitable for a catalytic hydrogenation reaction of acetylene in a product discharged in the conversion step.

An apparatus for converting a hydrocarbon-based material into acetylene or ethylene according to an embodiment of the present invention includes: a supply port configured to supply a gaseous or liquid hydrocarbon-based material; a reaction space configured to convert the hydrocarbon-based material into acetylene or ethylene through a plasma pyrolysis reaction by using a high temperature of a plasma arc; a discharge port configured to discharge the converted acetylene or ethylene; and an enlarged space further enlarged than the discharge port and configured to stop a hydrocarbon conversion reaction.

The apparatus may include: a housing having the supply port; a high-voltage electrode embedded at one side of the housing and disposed at a center of the supply port, the high-voltage electrode being configured to define a movement passage through which the hydrocarbon-based material moves, the movement passage being provided between the high-voltage electrode and an inner wall of the housing; a ground electrode spaced apart forward from the high-voltage electrode and configured to define an electric discharge gap between the ground electrode and the high-voltage electrode, the ground electrode being configured to define an inner passageway connected to the electric discharge gap and having a narrower width than an inner surface of the housing, the discharge port being provided at an end of the inner passageway; and an enlarged member connected to the ground electrode and configured to define the enlarged space.

The reaction space may be defined by the movement passage, the electric discharge gap, and the inner passageway.

The apparatus may further include an injection nozzle installed in the enlarged member and configured to inject a cooling fluid into the enlarged space.

The apparatus may include: a high-voltage electrode configured to define, at a center thereof, a movement passage through which the hydrocarbon-based material moves, and having the supply port at a tip of the movement passage; and a ground electrode spaced apart forward from the high-voltage electrode and configured to define an electric discharge gap between the ground electrode and the high-voltage electrode, the ground electrode being configured to define an inner passageway connected to the movement passage and the electric discharge gap, the discharge port being provided at an end of the inner passageway.

The apparatus may further include an insulator disposed between the high-voltage electrode and the ground electrode, and the insulator may define a connection passageway that connects the movement passage and the inner passageway.

The apparatus may include: a housing; a high-voltage electrode disposed at one side of the housing and configured to define a movement passage through which the hydrocarbon-based material moves, the movement passage having a doughnut structure, and the supply port being provided at a tip of the movement passage; and a ground electrode spaced apart forward from the high-voltage electrode and configured to define an electric discharge gap between the ground electrode and the high-voltage electrode, the ground electrode being configured to define an inner passageway connected to the electric discharge gap and having a narrower width than an inner surface of the housing, the discharge port being provided at an end of the inner passageway.

The apparatus may further include a catalyst part configured to raise a yield of ethylene by performing catalytic hydrogenation on acetylene in a product discharged from the enlarged space.

The catalyst part may include a heat exchange part configured to create a temperature condition suitable for the catalytic hydrogenation reaction.

Advantageous Effect

According to the embodiment of the present invention described above, hydrocarbon-based material (containing various types of hydrocarbon materials such as methane) is supplied to the plasma reactor, such that the temperature condition for the decomposition reaction of converting hydrocarbon-based material into acetylene or ethylene is created, and the temperature condition is maintained for the effective reaction time. Therefore, the hydrocarbon-based material may be converted directly into the acetylene or ethylene in the reaction space in the plasma reactor.

In the embodiment of the present invention, when the decrease in temperature of the reaction space is induced by maintaining the temperature condition for the effective reaction time in the quenching step, it is possible to effectively create the process condition with the temperature range (e.g., 1,000 to 2,500° C.) and the effective reaction time (e.g., 20 ms or less) of the decomposition reaction. Therefore, a hydrocarbon-based material (containing various types of hydrocarbon materials such as methane) may be converted into acetylene or ethylene.

MODE FOR INVENTION

Figure 1:
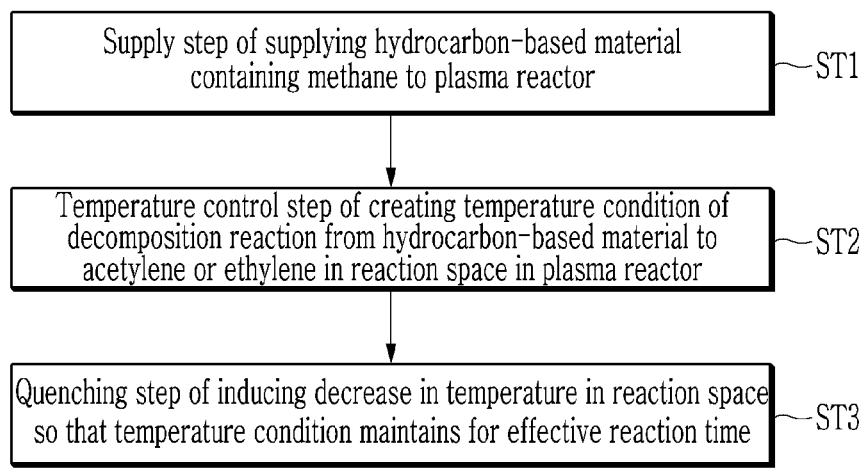
FIG. 1 is a flowchart illustrating a method of converting a hydrocarbon-based material into acetylene or ethylene according to a first embodiment of the present invention.

Hereinafter, embodiments of the present invention will be described in detail with reference to the accompanying drawings so that those with ordinary skill in the art to which the present invention pertains may easily carry out the embodiments. However, the present invention may be implemented in various different ways and is not limited to the embodiments described herein. In the drawings, a part irrelevant to the description will be omitted to clearly describe the present invention, and the same or similar constituent elements will be designated by the same reference numerals throughout the specification.

FIG. 1 is a flowchart illustrating a method of converting a hydrocarbon-based material into acetylene or ethylene according to a first embodiment of the present invention. Referring to FIG. 1, a first embodiment includes a supply step ST1, a temperature control step ST2, and a quenching step ST3.

In the supply step ST1, a gaseous or liquid hydrocarbon-based material containing various types of hydrocarbon materials such as methane is supplied to a conversion apparatus, i.e., first, second, third, and fourth plasma reactors 1, 2, 3, and 4 (see FIGS. 2 to 5). In the temperature control step ST2, a temperature condition suitable for a decomposition reaction of the hydrocarbon-based material is created in a reaction space in the plasma reactor.

Figure 2:
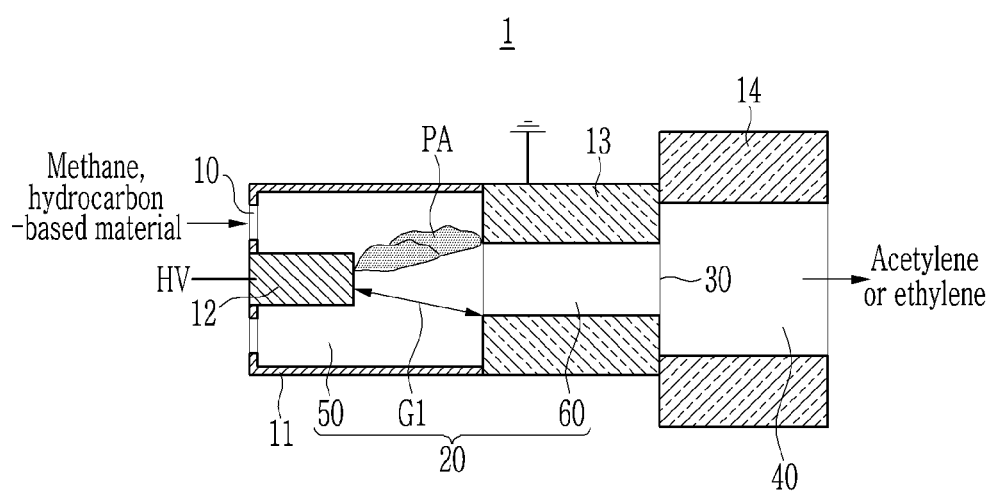
FIG. 2 is a cross-sectional view illustrating an apparatus for converting a hydrocarbon-based material into acetylene or ethylene according to the first embodiment of the present invention.

FIG. 2 is a cross-sectional view illustrating an apparatus for converting a hydrocarbon-based material into acetylene or ethylene according to the first embodiment of the present invention. Referring to FIG. 2, the conversion apparatus according to the first embodiment, i.e., the first plasma reactor 1 includes a supply port 10, a reaction space 20, a discharge port 30, and an enlarged space 40.

The supply port 10 is provided at one side of the first plasma reactor 1, and the gaseous or liquid hydrocarbon-based material containing methane is supplied through the supply port 10. The hydrocarbon-based material containing methane is used as plasma reactant gas.

The reaction space 20 is defined between the supply port 10 and the discharge port 30 of the first plasma reactor 1. In the reaction space 20, the hydrocarbon-based material is converted into acetylene or ethylene by a high temperature of a plasma arc PA through a plasma pyrolysis reaction.

The discharge port 30 discharges acetylene or ethylene converted in the reaction space 20. The enlarged space 40 is further expanded than the discharge port 30 and stops the hydrocarbon conversion reaction, thereby preventing the converted acetylene or ethylene from being converted into solid carbon.

More specifically, the first plasma reactor 1 includes a housing 11 having the supply port 10, a high-voltage electrode 12 configured to generate a plasma arc, a ground electrode 13, and an enlarged member 14.

The high-voltage electrode 12 is embedded at one side of the housing 11 and disposed at a center of the supply port 10 and defines a movement passage 50 through which the hydrocarbon-based material moves, and the movement passage 50 is provided between the high-voltage electrode 12 and an inner wall of the housing 11. High-voltage electric power HV is applied to the high-voltage electrode 12 to perform the conversion reaction. The high-voltage electric power HV may be direct current or alternating current.

The ground electrode 13 is spaced apart forward from the high-voltage electrode 12 and defines an electric discharge gap G1 between the ground electrode 13 and the high-voltage electrode 12. The ground electrode 13 defines an inner passageway 60 connected to the electric discharge gap G1 and having a narrower width than an inner surface of the housing 11. The discharge port 30 is provided at the end of the inner passageway 60. The inner passageway 60 of the ground electrode 13 is smaller and longer than an inner diameter of the housing 11, which defines the electric discharge gap G1, thereby forming a high-temperature reaction space. The ground electrode 13 is electrically grounded for the conversion reaction.

The enlarged member 14 is connected to the ground electrode 13 and defines the enlarged space 40. The enlarged member 14 is enlarged at one side of the discharge port 30 and larger than an inner diameter of the discharge port 30. The enlarged member 14 cools the high-temperature material, thereby terminating the high-temperature reaction space connected to the inner passageway 60.

Therefore, the reaction space 20 is defined by the movement passage 50, the electric discharge gap G1, and the inner passageway 60. A substantial hydrocarbon conversion reaction occurs in the inner passageway 60, and the hydrocarbon conversion reaction is stopped in the enlarged space 40.

That is, the hydrocarbon-based material containing methane is introduced into the supply port 10 and converted into acetylene or ethylene while passing through the movement passage 50, the electric discharge gap G1, and the inner passageway 60, and the acetylene or ethylene is discharged through the discharge port 30 to the enlarged space 40 and cooled. Therefore, the converted acetylene or ethylene may be obtained.

Referring back to FIGS. 1 and 2, in the temperature control step ST2, a temperature condition in the reaction space 20 or the inner passageway 60 may be created to be 1,000 to 2,500° C. In the temperature control step ST2, it is possible to create the temperature condition suitable for a condition for creating acetylene ($C_2H_2$) or ethylene ($C_2H_4$) by using the fact that a temperature of the reaction space 20 varies when the electric power is supplied to the high-voltage electrode 12 of the first plasma reactor 1 to produce the plasma arc PA. In the temperature control step ST2, the temperature of the reaction space 20 may vary depending on a length of the plasma arc PA.

In the temperature control step ST2, the alternating-current power or direct-current power may be applied to the high-voltage electrode 12 and the ground electrode 13 of the first plasma reactor 1. The length of the plasma arc PA may further increase when the alternating current power is applied than when the direct-current power is applied. In the temperature control step ST2, as the length of the plasma arc PA is maintained with elongated length, the plasma arc PA may be anchored to the inner passageway 60 of the ground electrode 13.

In the temperature control step ST2, electric discharge gas may be supplied with swirling flow for the plasma arc PA, and rotational momentum of the electric discharge gas may further stabilize the plasma arc PA. The first plasma reactor 1 and the embodiment uses the hydrocarbon-based material containing methane as the electric discharge gas.

In the temperature control step ST2, a temperature condition equal to or higher than a preset temperature is required to convert methane into acetylene or ethylene, and it is possible to create the temperature condition that is as low as possible and satisfies the temperature condition higher than the preset temperature. The length of the plasma arc PA is controlled by controlling the electric power to be applied to the high-voltage electrode 12 and the ground electrode 13. Therefore, it is possible to create the temperature condition required for the reaction space 20.

In the quenching step ST3, a decrease in temperature of the reaction space 20 is induced so that the temperature condition is maintained for an effective reaction time. In the quenching step ST3, the reaction time may be set by the length of the inner passageway 60, and thus the time for which the material is discharged from the reaction space 20 to the enlarged space 40 may be adjusted, thereby inducing a decrease in temperature of acetylene or ethylene converted from methane. For example, in the quenching step ST3, the quenching may be performed by the connection between the reaction space 20 or the inner passageway 60 and the enlarged space 40, thereby maintaining the reaction time within 20 ms or less.

In the quenching step ST3, a temperature of a reaction field formed in the reaction space 20 or the inner passageway 60 may be decreased in the enlarged space 40 to prevent the plasma pyrolysis reaction from being continuously performed. For example, in the quenching step ST3, the quenching is performed by cooling the wall surface of the enlarged space 40 connected to the reaction space 20 or the inner passageway 60, and the amount of cooling may be increased by increasing a surface area of the enlarged space 40 relative to a volume of the reaction space 20 or the inner passageway 60.

In the quenching step ST3, the temperature of the reaction field in the reaction space 20 or the inner passageway 60 may be a minimum temperature capable of maintaining the plasma pyrolysis reaction, and a temperature of a reaction emission (acetylene or ethylene converted from methane) may be lowered to a temperature, which is equal to or lower than the temperature that enables the pyrolysis reaction, by the structure or fluid-dynamics method of the first plasma reactor 1 that defines the enlarged space 40 at the end of the reaction field, i.e., the end of the inner passageway 60.

For example, acetylene may be formed by converting methane when thermodynamic equilibrium is a high-temperature condition (temperature control step) of 1,000° C. or higher, and the quenching (quenching step) is performed under the reaction condition for a short period of time of 10 ms or less. In this case, an appropriate amount of hydrogen is supplied together with methane. When the amount of supplied energy decreases (electric power applied to the high-voltage electrode 12 of the plasma reactor 1 decreases), ethylene may be produced as a main product.

In this case, unless the reaction under a high-temperature condition is quenched within a short time, solid carbon is produced from a part of acetylene or ethylene converted from methane, and a yield of acetylene or ethylene decreases. Further, it is difficult to continuously perform the reaction of converting methane.

However, a catalyst is sintered under the high-temperature condition, and the performance of the catalyst decreases. Because the catalyst and the support body have thermal mass, it is significantly difficult to quench the reaction under the high-temperature condition through the catalyst reaction within a short time. Therefore, the quenching using the catalyst cannot be applied.

In contrast, the first plasma reactor 1 applied to the embodiment may perform the reaction under the high-temperature condition by using plasma and perform the quenching under an appropriate temperature condition. The hydrocarbon-based material may pass through the reaction space 20 or the inner passageway 60 under the high-temperature condition of the plasma within a very short time, thereby reducing the temperature condition of the hydrocarbon-based material to a quenching condition or lower under which the pyrolysis reaction is not performed any further.

If it is possible to decrease the temperature condition of the hydrocarbon-based material to the quenching condition or less, the plasma may be produced only by the hydrocarbon-based material containing methane and hydrogen which are feed materials of the methane conversion reaction. That is, separate electric discharge gas for plasma discharge is not required. However, unless the electric discharge gas, i.e., the plasma source capable of controlling the temperature condition, i.e., the thermal environment of the methane conversion reaction is provided, it is difficult to relatively shorten the reaction time and produce acetylene or ethylene.

For example, when methane is supplied to high-frequency inductively coupled plasma (ICP), it is difficult to quickly quench the reaction, instability of the generation of plasma increases, and the plasma itself is quenched. That is, the high-frequency inductively coupled plasma cannot be used for the plasma reactor and the temperature control step.

In the embodiment, the plasma arc PA is produced within a very short time by relatively controlling the voltage and the electric current condition of the high-voltage electrode 12 at the time of producing the plasma arc PA. The temperature of the reaction space 20 or the inner passageway 60 is rapidly decreased in the enlarged space 40 through heat transfer in the plasma arc PA, such that the pyrolysis reaction in the reaction space 20 or the inner passageway 60 is quenched.

Figure 9:
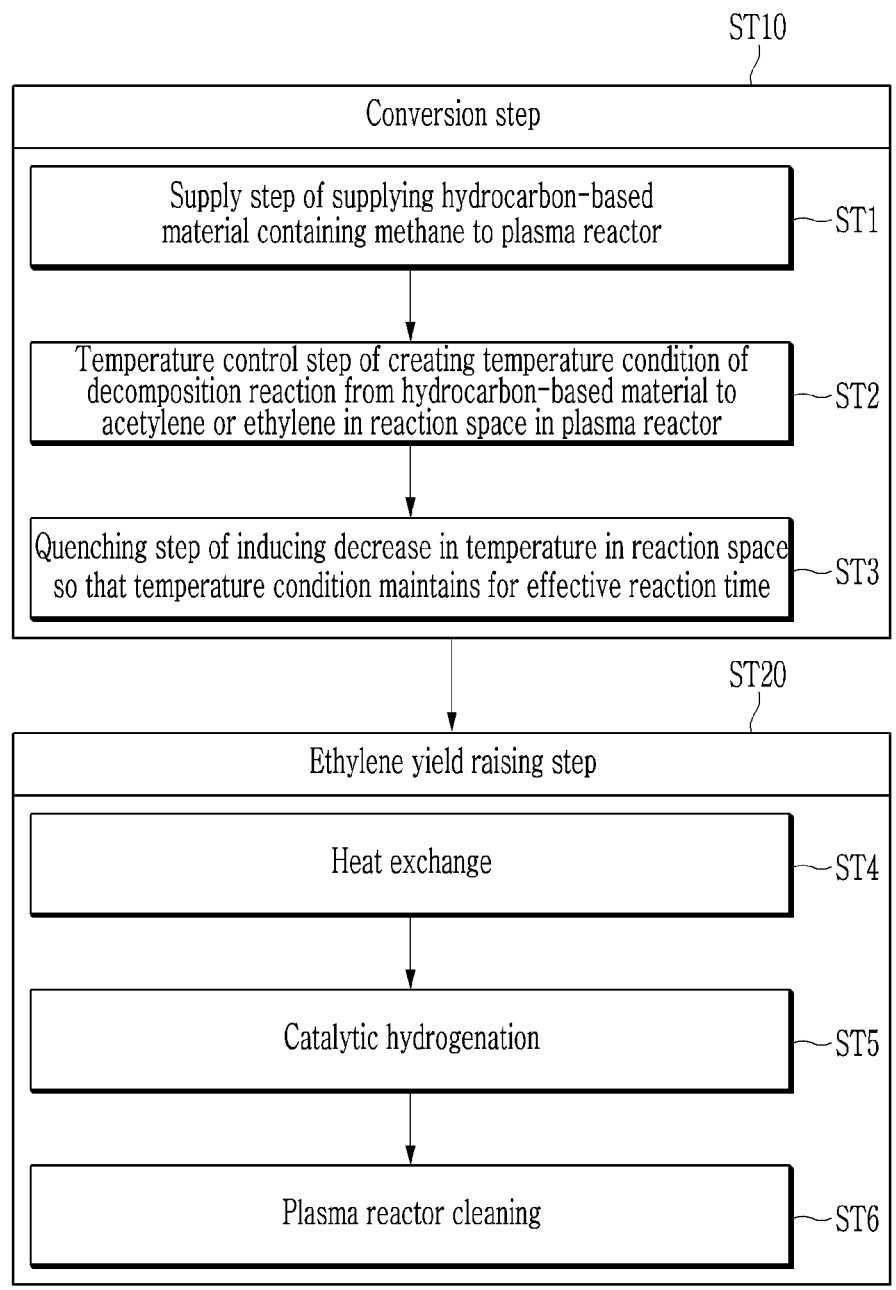
FIG. 9 is a flowchart illustrating a method of converting a hydrocarbon-based material into acetylene or ethylene according to the second embodiment of the present invention.

Meanwhile, in the first embodiment, the method may further include a plasma cleaning step ST6 of cleaning the plasma reactor 1 after the quenching step ST3 (see FIG. 9). When the plasma reactor 1 operates over a long period of time, there is a likelihood that the generated carbon is accumulated in the plasma reactor 1. In consideration of this likelihood, in the cleaning step ST6, carbon accumulated in the plasma reactor 1 is removed by a regeneration operation of stopping the periodical supply of the hydrocarbon-based material and supplying gas stream containing air or oxygen.

Hereinafter, various embodiments according to the present invention will be described. The description of the components, which are identical to the components of the conversion apparatus according to the first embodiment and the components of the conversion apparatuses according to the previously described embodiments, will be omitted, and the components different from the components of the conversion apparatus according to the first embodiment and the components of the conversion apparatuses according to the previously described embodiments will be described.

Figure 3:
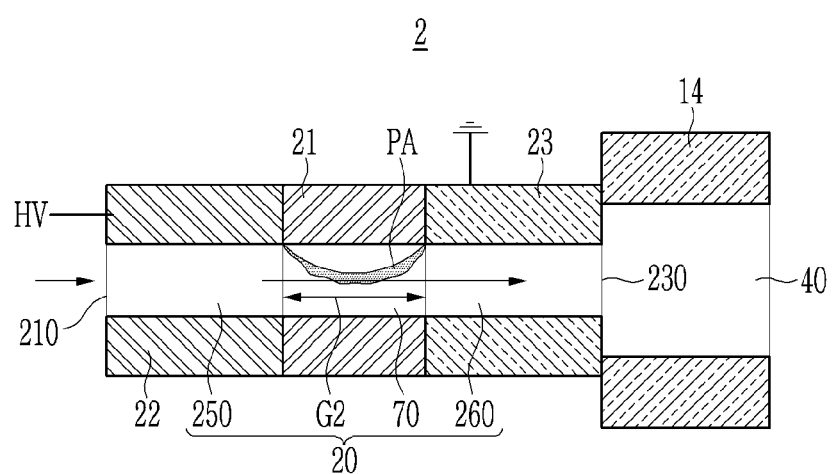
FIG. 3 is a cross-sectional view illustrating an apparatus for converting a hydrocarbon-based material into acetylene or ethylene according to a second embodiment of the present invention.

FIG. 3 is a cross-sectional view illustrating an apparatus for converting a hydrocarbon-based material into acetylene or ethylene according to a second embodiment of the present invention. Referring to FIG. 3, a conversion apparatus according to a second embodiment, i.e., a second plasma reactor 2 includes a high-voltage electrode 22, a ground electrode 23, and an insulator 21.

The high-voltage electrode 22 has at a center thereof, a movement passage 250 through which the hydrocarbon-based material moves, and a supply port 210 is provided at a tip of the movement passage 250. The ground electrode 23 is spaced apart forward from the high-voltage electrode 22 and defines an electric discharge gap G2 between the ground electrode 23 and the high-voltage electrode 12. The ground electrode 23 defines an inner passageway 260 connected to the movement passage 250 and the electric discharge gap G2, and a discharge port 230 is provided at the end of the inner passageway 260.

The high-voltage electrode 22 and the ground electrode 23 may form cylindrical surface discharge, thereby producing plasma arc PA2 having a larger volume than the plasma arc of the first embodiment. The second plasma reactor 2 may further increase a capacity of converting methane into acetylene ($C_2H_2$) or ethylene ($C_2H_4$) than the first plasma reactor 1.

The insulator 21 is disposed between the high-voltage electrode 22 and the ground electrode 23. The insulator 21 further defines a connection passageway 70 that connects the movement passage 250 and the inner passageway 260. In this case, a reaction space 220 is defined by the movement passage 250, the connection passageway 70 of the electric discharge gap G2, and the inner passageway 260. A substantial hydrocarbon conversion reaction occurs in the inner passageway 260, and the hydrocarbon conversion reaction is stopped in the enlarged space 40.

In the temperature control step ST2, it is possible to create the temperature condition suitable for a condition for creating acetylene ($C_2H_2$) or ethylene ($C_2H_4$) by using the fact that a temperature of the reaction space 220 varies when the same electric power is supplied to the high-voltage electrode 22 of the second plasma reactor 2 to produce the plasma arc PA2. In the temperature control step ST2, the temperature of the reaction space 220 may vary depending on a length of the plasma arc PA2.

In the temperature control step ST2, the alternating-current power or direct-current power may be applied to the high-voltage electrode 22 and the ground electrode 23 of the second plasma reactor 2. The length of the plasma arc PA2 may further increase when the alternating-current power is applied than when the direct-current power is applied. In the temperature control step ST2, as the length of the plasma arc PA2 is maintained with elongated length, the plasma arc PA2 may be anchored to the inner passageway 260 of the ground electrode 23 and stabilized.

Figure 4:
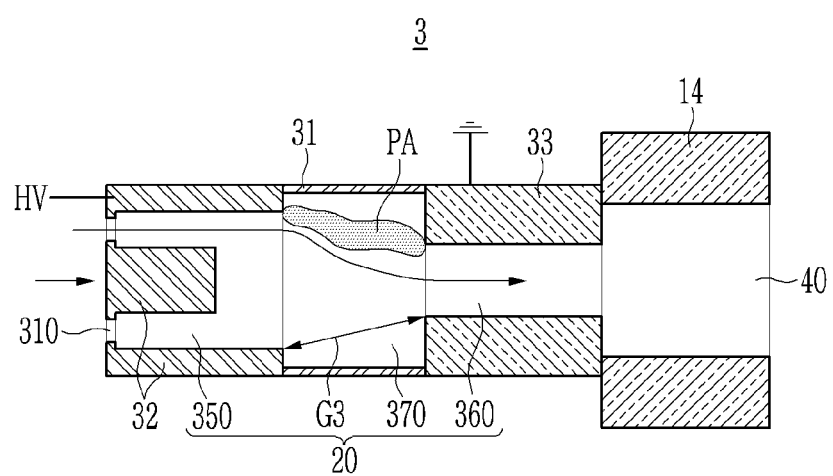
FIG. 4 is a cross-sectional view illustrating an apparatus for converting a hydrocarbon-based material into acetylene or ethylene according to a third embodiment of the present invention.

FIG. 4 is a cross-sectional view illustrating an apparatus for converting a hydrocarbon-based material into acetylene or ethylene according to a third embodiment of the present invention. Referring to FIG. 4, a conversion apparatus according to a third embodiment, i.e., a third plasma reactor 3 includes a housing 31, a high-voltage electrode 32, and a ground electrode 33.

For example, the housing 31 has a cylindrical shape. The high-voltage electrode 32 is disposed at one side of the housing 31, and a movement passage 350 through which the hydrocarbon-based material moves has a doughnut structure. A supply port 310 is provided at a tip of the movement passage 350.

The ground electrode 33 defines an electric discharge gap G3 at a front side of the high-voltage electrode 32. The ground electrode 33 defines an inner passageway 360 connected to the electric discharge gap G3 and having a narrower width than an inner surface of the housing 31. A discharge port 330 is provided at the end of the inner passageway 360.

The high-voltage electrode 32 and the ground electrode 33 may form surface discharge having a truncated conical shape, thereby producing plasma arc PA3 having a larger volume than the plasma arc of the first embodiment. The third plasma reactor 3 may further increase a capacity of converting methane into acetylene ($C_2H_2$) or ethylene ($C_2H_4$) than the first plasma reactor 1.

The housing 31 is disposed between the high-voltage electrode 32 and the ground electrode 33. The housing 31 further defines a connection passageway 370 that connects the movement passage 350 and the inner passageway 360. In this case, a reaction space 320 is defined by the movement passage 350, the connection passageway 370 of the electric discharge gap G3, and the inner passageway 360. A substantial conversion reaction occurs in the inner passageway 360, and the hydrocarbon conversion reaction is stopped in the enlarged space 40.

In the temperature control step ST2, it is possible to create the temperature condition suitable for a condition for creating acetylene ($C_2H_2$) or ethylene ($C_2H_4$) by using the fact that a temperature of the reaction space 320 varies when the same electric power is supplied to the high-voltage electrode 32 of the third plasma reactor 3 to produce the plasma arc PA3. In the temperature control step ST2, the temperature of the reaction space 320 may vary depending on a length of the plasma arc PA3.

In the temperature control step ST2, the alternating-current power or direct-current power may be applied to the high-voltage electrode 32 and the ground electrode 33 of the third plasma reactor 3. The length of the plasma arc PA3 may further increase when the alternating-current power is applied than when the direct-current power is applied. In the temperature control step ST2, as the length of the plasma arc PA3 is maintained with elongated length, the plasma arc PA3 may be anchored to the inner passageway 360 of the ground electrode 33.

Figure 5:
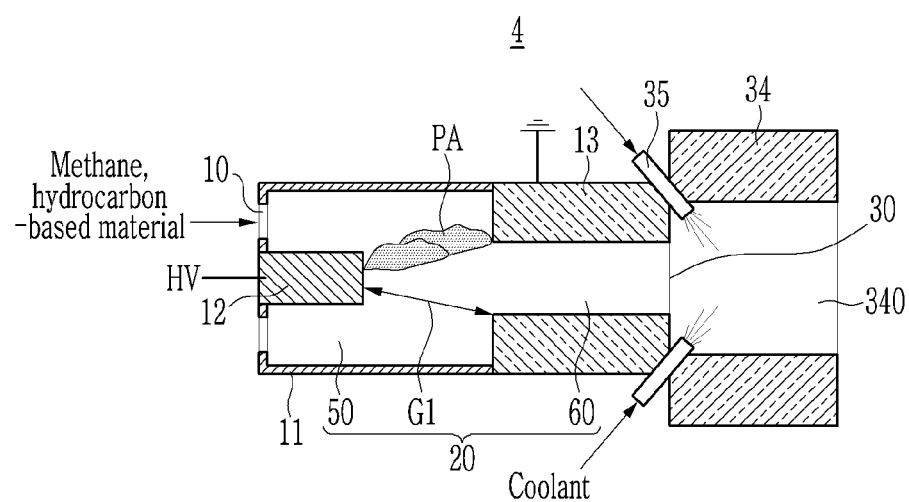
FIG. 5 is a cross-sectional view illustrating an apparatus for converting a hydrocarbon-based material into acetylene or ethylene according to a fourth embodiment of the present invention.

FIG. 5 is a cross-sectional view illustrating an apparatus for converting a hydrocarbon-based material into acetylene or ethylene according to a fourth embodiment of the present invention. Referring to FIG. 5, a conversion apparatus according to a fourth embodiment, i.e., a fourth plasma reactor 4 further includes an injection nozzle 35.

The injection nozzle 35 is installed in the enlarged member 34, injects a cooling fluid into the enlarged space 340, and quenches acetylene ($C_2H_2$) or ethylene ($C_2H_4$) converted from methane in the enlarged space 340, thereby preventing the converted acetylene or ethylene from being converted into solid carbon.

The fourth plasma reactor 4 according to the fourth embodiment is a modified example of the first plasma reactor 1 according to the first embodiment. Although not illustrated separately, the injection nozzle according to the fourth embodiment may be applied to the second and third plasma reactors 2 and 3 according to the second and third embodiments.

Meanwhile, an example of the method of converting a hydrocarbon-based material into acetylene or ethylene by applying the first, second, third, and fourth plasma reactors 1, 2, 3, and 4 will be described.

Figure 6:
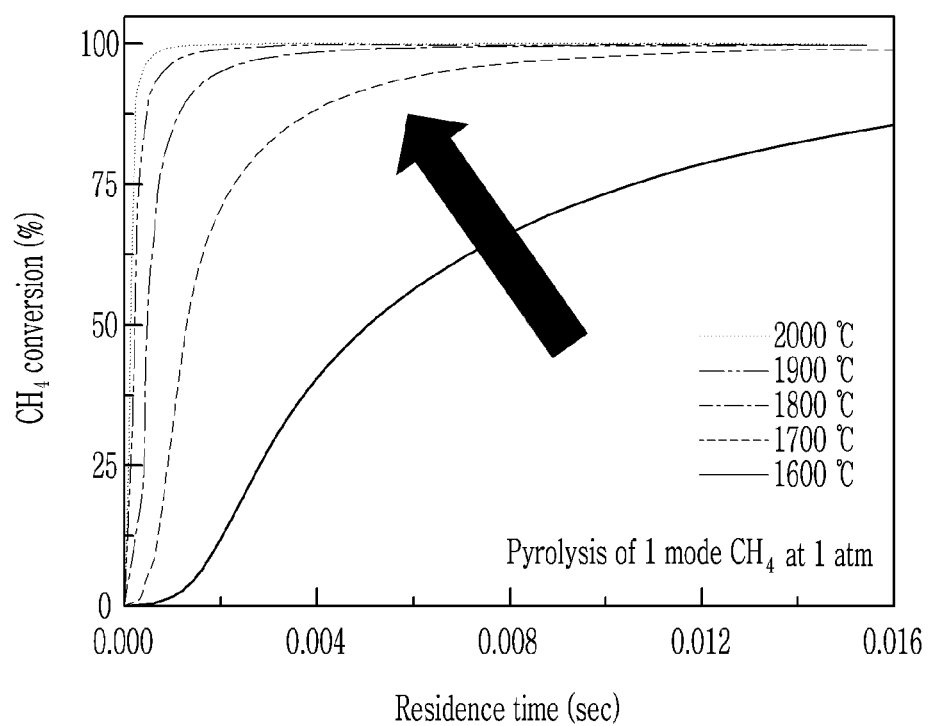
FIG. 6 is a graph illustrating a relationship between reaction time (sec) and a conversion ratio (%) of methane ($CH_4$) at the time of thermally decomposing one mole of methane at one atmospheric pressure.
Figure 7:
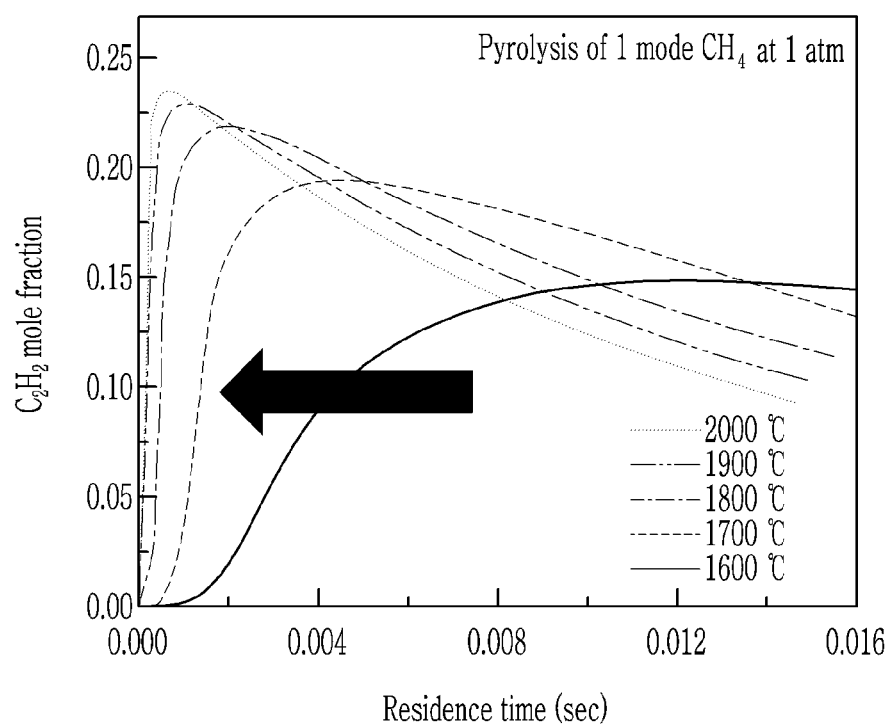
FIG. 7 is a graph illustrating a relationship between a reaction time and a mole fraction of acetylene ($C_2H_2$) at the time of thermally decomposing one mole of methane at one atmospheric pressure.

FIG. 6 is a graph illustrating a relationship between reaction time (sec) and a conversion ratio (%) of methane ($CH_4$) at the time of thermally decomposing one mole of methane at one atmospheric pressure, and FIG. 7 is a graph illustrating a relationship between a reaction time and a mole fraction of acetylene ($C_2H_2$) at the time of thermally decomposing one mole of methane at one atmospheric pressure.

Referring to the theoretically calculated value illustrated in FIGS. 6 and 7, the reaction time (residence time (RT)) needs to be $0 < RT \leq 6$ ms and the reaction temperature (conversion temperature (CT)) needs to be 1700° C. CT to produce a larger amount of acetylene ($C_2H_2$) from methane (CH$_4$). In consideration of the physical characteristics, the first, second, third, and fourth plasma reactors 1, 2, 3, and 4 applied to the present invention may provide the reaction time (RT) of 0<RT≤10 ms and the reaction temperature (CT) of 1,000≤CT≤2,500° C. That is, the first, second, third, and fourth plasma reactors 1, 2, 3, and 4 may provide the reaction time and reaction temperature condition wider than the theoretically calculated value.

To shorten the reaction time as described above, a large amount of energy needs to be supplied to a mechanical reactor (not illustrated) of a comparative example in order to heat the hydrocarbon-based material (e.g., methane) supplied at a high temperature. However, even though high energy is supplied to methane from the outside, there is a need for the time it takes for energy to be transferred to methane. For this reason, when the reaction time is set in a range of 0.5 ms or less in the typical mechanical reactor, the heat transfer is not sufficient, and the pyrolysis reaction cannot be smoothly performed.

A yield of a product (e.g., acetylene) is decreased by solid carbon produced by pyrolysis of methane at the time of obtaining acetylene (C$_2$H$_2$) by converting methane. Therefore, it is necessary to supply hydrogen together with methane and allow hydrogen and methane to react with each other to inhibit the generation of unnecessary solid carbon.

The first, second, third, and fourth plasma reactors 1, 2, 3, and 4 may operate within a range in which a ratio (H$_2$/CH$_4$) of hydrogen to methane is 1 to 9. The first plasma reactor 1 can hardly operate continuously because of an excessive amount of solid carbon when the ratio (H$_2$/CH$_4$) is less than 1 or more than 9.

Figure 8:
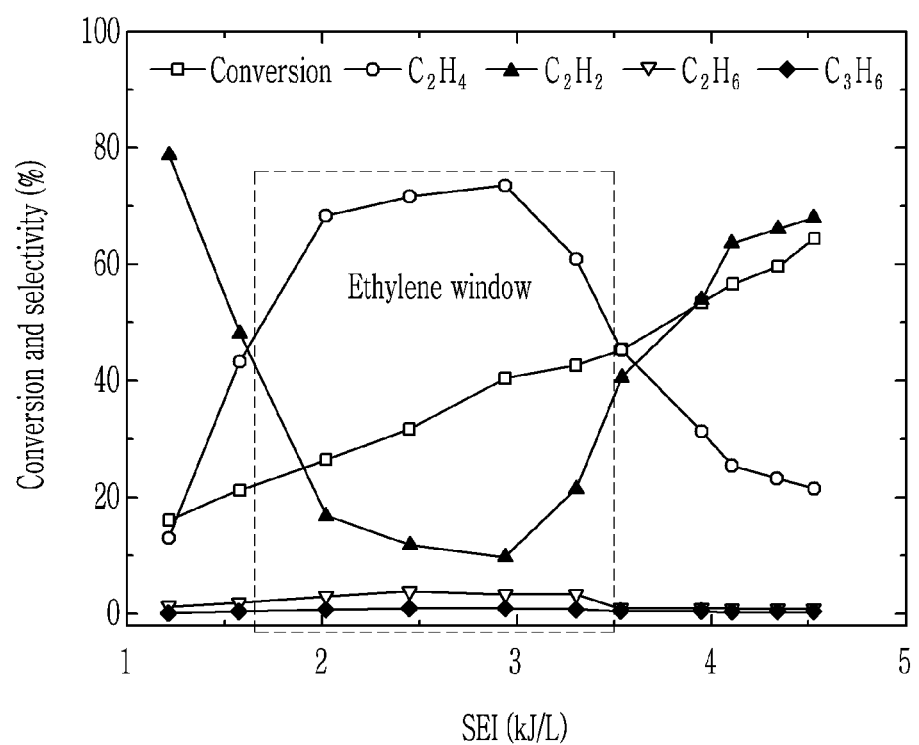
FIG. 8 is a graph illustrating a relationship between conversion and reaction selectivity and energy supplied to generate plasma (expressed by electrical energy supplied with respect to a unit flow rate of a hydrocarbon-based material (SEI=kJ/L)).

FIG. 8 is a graph illustrating a relationship between conversion and reaction selectivity and energy supplied to generate plasma (expressed by electrical energy supplied with respect to a unit flow rate of a hydrocarbon-based material (SEI=kJ/L)).

The energy (SEI=kJ/L) to be supplied to the first, second, third, and fourth plasma reactors 1, 2, 3, and 4 to increase the reaction temperature for the reaction of the supplied hydrocarbon-based material (e.g., methane) may be expressed by electrical energy (kJ) supplied per unit flow rate (Liter) of the hydrocarbon-based material.

The composition of the products is changed by actually reacting the hydrocarbon-based material in a range of energy (SEI) value. For example, the main product is ethylene (C$_2$H$_4$) when the hydrocarbon-based material, of which the ratio (H$_2$/CH$_4$) of hydrogen to methane is within a range of 1 to 9, is supplied, and the energy (SEI) supplied in FIG. 8 is 2 to 3.5. When the ratio is more than 3.5, the main product is acetylene (C$_2$H$_2$).

For example, when selectivity of ethylene (C$_2$H$_4$) is 80% at the time of converting methane, 80% of carbon in the converted methane is converted into ethylene. Further, when energy (SEI) is 1.5 or less, energy to be supplied to the first, second, third, and fourth plasma reactors 1, 2, 3, and 4 is insufficient. Therefore, the conversion of methane itself is meaningless.

The key to the reaction for producing C2 compound (acetylene, ethylene) by converting methane is to create the reaction temperature (CT) of 1,700° C.≤CT by supplying sufficient heat within the reaction time (RT), which is as short as RT≤10 ms, and then reducing, within a short time, a temperature to a temperature at which the pyrolysis reaction is not performed any further.

High energy (SEI) of 2 to 3.5 cannot be applied within the short reaction time (RT) of RT≤10 ms except for the plasma produced by the first, second, third, and fourth plasma reactors 1, 2, 3, and 4. A size of each of the first, second, third, and fourth plasma reactors 1, 2, 3, and 4 is a radius R of the reaction space, and the reaction needs to be performed within the following condition in respect to a flow velocity Q of the supplied hydrocarbon-based material and a length L of the reaction space (unit=second).

$$0.0005 < \frac{L \cdot \pi R^2}{Q} < 0.01$$

Hereinafter, the conversion method according to the second embodiment will be described. Referring to the comparison between the conversion method according to the first embodiment and the conversion method according to the second embodiment, the description of the same configuration will be omitted, and different configurations will be described.

FIG. 9 is a flowchart illustrating a method of converting a hydrocarbon-based material into acetylene or ethylene according to the second embodiment of the present invention. Referring to FIG. 9, the conversion method according to the second embodiment includes a conversion step ST10 and an ethylene yield raising step ST20.

Figure 10:
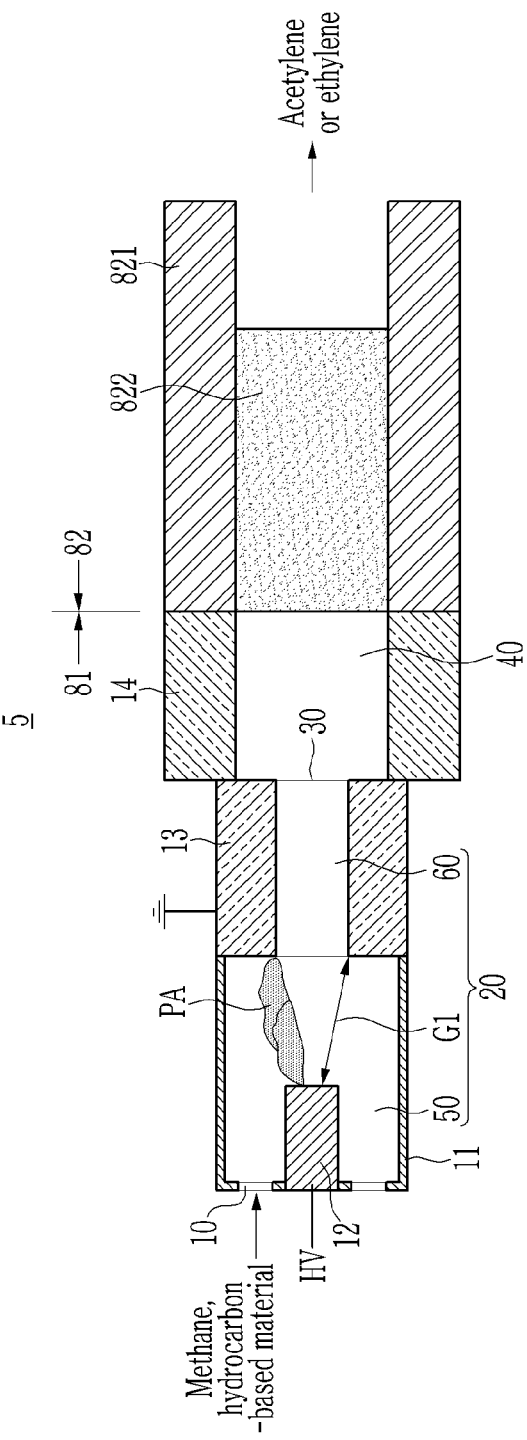
FIG. 10 is a cross-sectional view illustrating an apparatus for converting a hydrocarbon-based material into acetylene or ethylene according to a fifth embodiment of the present invention.

FIG. 10 is a cross-sectional view illustrating an apparatus for converting a hydrocarbon-based material into acetylene or ethylene according to a fifth embodiment of the present invention. Referring to FIG. 10, a conversion apparatus according to a fifth embodiment, i.e., a plasma reactor 5 includes a conversion part 81 and a catalyst part 82.

The conversion part 81 serves to convert a gaseous or liquid hydrocarbon-based material into acetylene or ethylene. The conversion part 81 may be configured as the plasma reactor 1 according to the first embodiment.

The catalyst part 82 serves to raise a yield of ethylene by performing catalytic hydrogenation on acetylene produced by the conversion part 81. The plasma reactor 5 according to the fifth embodiment further includes the catalyst part 82 in comparison with the plasma reactor 1 according to the first embodiment.

The catalyst part 82 has a catalyst 822 provided in the catalyst housing 821. The catalyst housing 821 is connected to the enlarged member 14. Therefore, the product containing acetylene and ethylene, which passes through the enlarged member 14, passes through the catalyst 822 embedded in the catalyst housing 821.

Referring to FIGS. 9 and 10, in the conversion step ST10, the high-temperature plasma in the plasma reactor 5 converts the gaseous or liquid hydrocarbon-based material into acetylene or ethylene through the decomposition reaction. For example, in the conversion step ST10, the hydrocarbon-based material may be converted into acetylene or ethylene by the first, second, and third steps ST1, ST2, and ST3 according to the first embodiment.

In the ethylene yield raising step ST20, the acetylene produced in the conversion step ST10 passes through the catalyst part 82, such that ethylene is additionally produced, which makes it possible to raise a yield of ethylene. For example, in the ethylene yield raising step ST20, a yield of ethylene may be raised in a catalytic hydrogenation step ST5.

The ethylene yield raising step ST20 may further include the plasma reactor cleaning step ST6 of cleaning the plasma reactor 5. When the plasma reactor 5 operates over a long period of time, there is a likelihood that the generated carbon is accumulated in the plasma reactor 5. In consideration of this likelihood, in the cleaning step ST6, carbon accumulated in the plasma reactor 5 is removed by a regeneration operation of stopping the periodical supply of the hydrocarbon-based material and supplying gas stream containing air or oxygen. The catalyst 822 embedded in the catalyst part 82 may be regenerated by the regeneration operation in the cleaning step ST6.

Figure 11:
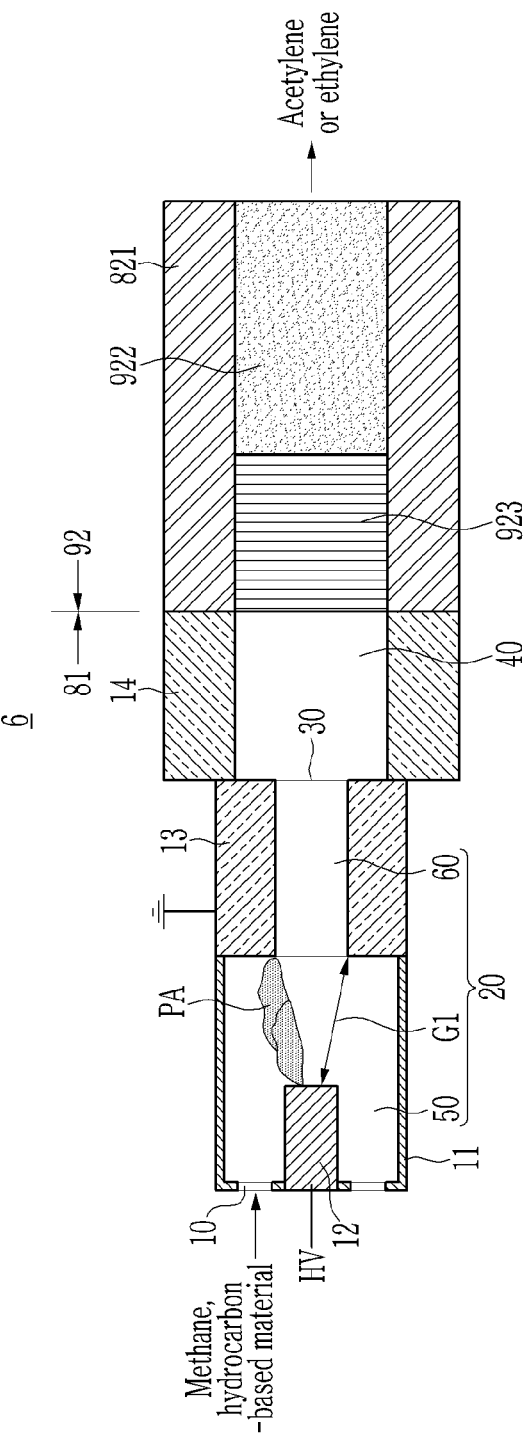
FIG. 11 is a cross-sectional view illustrating an apparatus for converting a hydrocarbon-based material into acetylene or ethylene according to a sixth embodiment of the present invention.

FIG. 11 is a cross-sectional view illustrating an apparatus for converting a hydrocarbon-based material into acetylene or ethylene according to a sixth embodiment of the present invention. Referring to FIG. 11, a conversion apparatus according to a sixth embodiment, i.e., a plasma reactor 6 includes the conversion part 81 and a catalyst part 92. The catalyst part 92 has a catalyst 922 and a heat exchange part 923 embedded in the catalyst housing 821.

The heat exchange part 923 creates a temperature condition of the catalyst part 92 so that a product containing acetylene and ethylene discharged from the conversion part 81 of the plasma reactor 6 is suitable for the catalyst reaction of the catalyst 922 in the catalyst part 92. For example, the heat exchange part 923 may be configured as a heater or cooling device depending on a required reaction temperature.

In a case in which the heat exchange part 923 is provided, the ethylene yield raising step ST20 may further include a heat exchange step ST4 before the catalytic hydrogenation step ST5. The heat exchange step ST4 forms the temperature condition first which is suitable for the catalytic hydrogenation reaction of acetylene in the product discharged in the conversion step ST10. Therefore, it is possible to further raise a yield when acetylene is converted into ethylene at the catalyst 922 in the catalyst part 92.

While the exemplary embodiments of the present invention have been described above, the present invention is not limited thereto, and various modifications can be made and carried out within the scope of the claims, the detailed description of the invention, and the accompanying drawings, and also fall within the scope of the invention.

DESCRIPTION OF REFERENCE NUMERALS 1, 2, 3, 4, 5, and 6: First, second, third, fourth, fifth, and sixth plasma reactors
10, 210, 310: Supply port 11, 31: Housing
12, 22, 32: High-voltage electrode
13, 23, 33: Ground electrode
14, 34: Enlarged member 20, 220, 320: Reaction space
21: Insulator 30, 230, 330: Discharge port
35: Injection nozzle 40: Enlarged space
50, 250, 350: Movement passage
60, 260, 360: Inner passageway
70, 370: Connection passageway 81: Conversion part
82, 92: Catalyst part 821: Catalyst housing
822, 922: Catalyst 923: Heat exchange part
G1, G2, G3, G4: Electric discharge gap
HV: High-voltage electric power
PA, PA2, PA3: Plasma arc

The invention claimed is:

1. A method of converting a hydrocarbon-based material into acetylene or ethylene, the method comprising:
a supply step of supplying a gaseous or liquid hydrocarbon-based material to a plasma reactor;
a temperature control step of creating a temperature condition of a decomposition reaction of converting the hydrocarbon-based material into acetylene or ethylene in a reaction space in the plasma reactor; and
a quenching step of inducing a decrease in a temperature of the reaction space so that the temperature condition is only maintained for an effective reaction time in the temperature control step,
wherein the plasma reactor includes:
a high-voltage electrode being configured to define a movement passage through which the hydrocarbon-based material moves; and
a ground electrode spaced apart forward from the high-voltage electrode and configured to define an electric discharge gap between the ground electrode and the high-voltage electrode, the ground electrode being configured to define an inner passageway connected to the electric discharge gap, and
wherein the temperature control step comprises applying alternating current power or direct current power to the high-voltage electrode and the ground electrode of the plasma reactor to maintain a length of a plasma arc produced, thereby anchoring the plasma arc to the inner passageway of the ground electrode.

2. The method of claim 1, wherein:
the temperature control step comprises creating the temperature condition of the reaction space with a temperature range of 1,000 to 2,500° C.

3. The method of claim 2, wherein:
the quenching step comprises maintaining the reaction time to 20 ms or less by quenching the reaction space.

4. The method of claim 2, wherein:
in the temperature control step, the temperature of the reaction space varies depending on the length of the plasma arc when a same electric power is supplied to the plasma reactor to produce the plasma arc.

5. The method of claim 2, wherein:
the temperature control step comprises setting the temperature of the reaction space as low as possible while meeting a minimum temperature required to convert methane into acetylene or ethylene.

6. The method of claim 2, wherein:
in the temperature control step, the length of the plasma arc further increases when applying the alternating current power instead of the direct current power.

7. The method of claim 6, wherein:
the temperature control step comprises supplying an electric discharge gas with swirling flow for the plasma arc thereby stabilizing the plasma arc by means of a rotational momentum of the electric discharge gas.

8. The method of claim 3, wherein:
the quenching step comprises decreasing a temperature of a reaction field formed in the reaction space to prevent the decomposition reaction from being continuously performed.

9. The method of claim 8, wherein:
in the quenching step, the temperature of the reaction field is a minimum temperature capable of maintaining the decomposition reaction, and a temperature of a reaction emission is lowered to a temperature equal to or lower than a temperature that enables the decomposition reaction to be performed by a structure or fluid-dynamics method of the plasma reactor at an end of the reaction field.

10. The method of claim 1 further comprising:
raising a yield of ethylene by performing catalytic hydrogenation on acetylene produced,
wherein raising the yield of ethylene comprises a heat exchange step of creating a temperature condition suitable for a catalytic hydrogenation reaction of acetylene produced.

11. An apparatus for converting a hydrocarbon-based material into acetylene or ethylene, the apparatus comprising:
- a housing having a supply port configured to supply a gaseous or liquid hydrocarbon-based material;
- a reaction space configured to convert the hydrocarbon-based material into acetylene or ethylene through a plasma pyrolysis reaction by using a high temperature of a plasma arc;
- a discharge port configured to discharge the converted acetylene or ethylene;
- an enlarged space further enlarged than the discharge port and configured to stop a hydrocarbon conversion reaction;
- a high-voltage electrode embedded at one side of the housing and disposed at a center of the supply port, the high-voltage electrode being configured to define a movement passage through which the hydrocarbon-based material moves, the movement passage being provided between the high-voltage electrode and an inner wall of the housing;
- a ground electrode spaced apart forward from the high-voltage electrode and configured to define an electric discharge gap between the ground electrode and the high-voltage electrode, the ground electrode being configured to define an inner passageway connected to the electric discharge gap and having a narrower width than an inner surface of the housing, the discharge port being provided at an end of the inner passageway.

12. The apparatus of claim 11, wherein:
the enlarged space is defined by an enlarged space connected to the ground electrode.

13. The apparatus of claim 12, wherein:
the reaction space is defined by the movement passage, the electric discharge gap, and the inner passageway.

14. The apparatus of claim 12, further comprising:
an injection nozzle installed in the enlarged member and configured to inject a cooling fluid into the enlarged space.

15. The apparatus of claim 11, further comprising:
a catalyst part configured to raise a yield of ethylene by performing catalytic hydrogenation on acetylene in a product discharged from the enlarged space.

16. The apparatus of claim 15, wherein:
the catalyst part comprises a heat exchange part configured to create a temperature condition suitable for the catalytic hydrogenation reaction.

17. An apparatus for converting a hydrocarbon-based material into acetylene or ethylene, the apparatus comprising:
- a supply port configured to supply a gaseous or liquid hydrocarbon-based material;
- a reaction space configured to convert the hydrocarbon-based material into acetylene or ethylene through a plasma pyrolysis reaction by using a high temperature of a plasma arc;
- a discharge port configured to discharge the converted acetylene or ethylene;
- an enlarged space further enlarged than the discharge port and configured to stop a hydrocarbon conversion reaction;
- a high-voltage electrode configured to define, at a center thereof, a movement passage through which the hydrocarbon-based material moves, and having the supply port at a tip of the movement passage; and
- a ground electrode spaced apart forward from the high-voltage electrode and configured to define an electric discharge gap between the ground electrode and the high-voltage electrode, the ground electrode being configured to define an inner passageway connected to the movement passage and the electric discharge gap, the discharge port being provided at an end of the inner passageway.

18. The apparatus of claim 17, further comprising:
an insulator disposed between the high-voltage electrode and the ground electrode,
wherein the insulator defines a connection passageway that connects the movement passage and the inner passageway.

19. An apparatus for converting a hydrocarbon-based material into acetylene or ethylene, the apparatus comprising:
- a supply port configured to supply a gaseous or liquid hydrocarbon-based material;
- a reaction space configured to convert the hydrocarbon-based material into acetylene or ethylene through a plasma pyrolysis reaction by using a high temperature of a plasma arc;
- a discharge port configured to discharge the converted acetylene or ethylene;
- an enlarged space further enlarged than the discharge port and configured to stop a hydrocarbon conversion reaction;
- a housing;
- a high-voltage electrode disposed at one side of the housing and configured to define a movement passage through which the hydrocarbon-based material moves, the movement passage having a doughnut structure, and the supply port being provided at a tip of the movement passage; and
- a ground electrode spaced apart forward from the high-voltage electrode and configured to define an electric discharge gap between the ground electrode and the high-voltage electrode, the ground electrode being configured to define an inner passageway connected to the electric discharge gap and having a narrower width than an inner surface of the housing, the discharge port being provided at an end of the inner passageway.

\* \* \* \* \*